(12) United States Patent
Yuchi et al.

(10) Patent No.: US 12,004,903 B2
(45) Date of Patent: Jun. 11, 2024

(54) SPIRAL ULTRASONIC TOMOGRAPHY IMAGING METHOD AND SYSTEM

(71) Applicant: HUAZHONG UNIVERSITY OF SCIENCE AND TECHNOLOGY, Hubei (CN)

(72) Inventors: Ming Yuchi, Hubei (CN); Mingyue Ding, Hubei (CN); Qiude Zhang, Hubei (CN); Junjie Song, Hubei (CN); Kuolin Liu, Hubei (CN); Zhaohui Liu, Hubei (CN); Liang Zhou, Hubei (CN); Zhaohui Quan, Hubei (CN); Xiaoyue Fang, Hubei (CN); Yun Wu, Hubei (CN); Quan Zhou, Hubei (CN)

(73) Assignee: HUAZHONG UNIVERSITY OF SCIENCE AND TECHNOLOGY, Hubei (CN)

( * ) Notice: Subject to any disclaimer, the term of this patent is extended or adjusted under 35 U.S.C. 154(b) by 6 days.

(21) Appl. No.: 17/274,789

(22) PCT Filed: Oct. 24, 2019

(86) PCT No.: PCT/CN2019/112997
§ 371 (c)(1),
(2) Date: Mar. 10, 2021

(87) PCT Pub. No.: WO2021/056655
PCT Pub. Date: Apr. 1, 2021

(65) Prior Publication Data
US 2021/0386398 A1  Dec. 16, 2021

(30) Foreign Application Priority Data
Sep. 29, 2019  (CN) .......................... 201910932901.7

(51) Int. Cl.
*A61B 8/14*  (2006.01)
*A61B 8/00*  (2006.01)
*A61B 8/08*  (2006.01)

(52) U.S. Cl.
CPC ............ *A61B 8/145* (2013.01); *A61B 8/4281* (2013.01); *A61B 8/4455* (2013.01); *A61B 8/4494* (2013.01); *A61B 8/5215* (2013.01)

(58) Field of Classification Search
CPC ..... A61B 8/145; A61B 8/4281; A61B 8/4455; A61B 8/4494; A61B 8/5215; A61B 8/4461; A61B 8/483; A61B 8/5207
See application file for complete search history.

(56) References Cited

U.S. PATENT DOCUMENTS

| | | | |
|---|---|---|---|
| 11,125,725 B2 * | 9/2021 | Kannajosyula | G01N 29/2437 |
| 2002/0045821 A1 * | 4/2002 | Tsuzuki | G01S 7/52025 |
| | | | 600/443 |

(Continued)

FOREIGN PATENT DOCUMENTS

| | | | | |
|---|---|---|---|---|
| FR | 2596156 A | * | 9/1987 | ......... G01S 15/8918 |
| FR | 2596156 A1 | * | 9/1987 | ......... G01S 15/8918 |

OTHER PUBLICATIONS

Tri-plane cardiac imaging using multi-line transmission on a spiral array: a feasibility study, Ramalli et al., 2018 IEEE International Ultrasonic Symposium (Year: 2018).*

(Continued)

*Primary Examiner* — Shahdeep Mohammed
*Assistant Examiner* — Fikirte (Fiki) T Ashine
(74) *Attorney, Agent, or Firm* — JCIP GLOBAL INC.

(57) ABSTRACT

A spiral ultrasonic tomography imaging method and system are provided. The method is to use synchronous rotation of an ultrasonic probe or cyclic switching of emission array elements in the ultrasonic probe under the premise of a uniform displacement of the ultrasonic probe along the Z axis, so that the change trajectory of the positions of emission array elements over time in a three-dimensional space at each ultrasonic emission time is distributed along a spiral line or a curve. During the process of the uniform displacement of the ultrasonic probe along the Z axis, the ultrasonic probe emits ultrasonic waves and receives and collects echo data. The collected echo data is stored and (Continued)

post-processed to realize ultrasonic tomography imaging of an object. The spiral ultrasonic tomography three-dimensional scanning method and the corresponding system realize rapid continuous uninterrupted data acquisition to ensure that higher spatial resolution in the Z-axis direction.

8 Claims, 6 Drawing Sheets

(56) References Cited

U.S. PATENT DOCUMENTS

| | | | | |
|---|---|---|---|---|
| 2008/0177180 | A1* | 7/2008 | Azhari | A61B 8/406 600/439 |
| 2011/0224548 | A1* | 9/2011 | Otaki | A61B 8/486 600/443 |
| 2012/0095343 | A1* | 4/2012 | Smith | A61B 8/58 600/447 |
| 2014/0342397 | A1* | 11/2014 | Andersen Gad | B01D 29/66 210/791 |

OTHER PUBLICATIONS

Ramalli et al.,. "Tri-plane cardiac imaging using multi-line transmission on a spiral array" IEEEE, Pub. 2018 (Year: 2018).*

* cited by examiner

SPIRAL ULTRASONIC TOMOGRAPHY IMAGING METHOD AND SYSTEM

CROSS-REFERENCE TO RELATED APPLICATION

This application is a 371 of international application of PCT application serial no. PCT/CN2019/112997, filed on Oct. 24, 2019, which claims the priority benefit of China application no. 201910932901.7, filed on Sep. 29, 2019. The entirety of each of the above mentioned patent applications is hereby incorporated by reference herein and made a part of this specification.

BACKGROUND

Technical Field

The disclosure belongs to the field of ultrasound imaging, and more specifically relates to a spiral ultrasonic tomography imaging method and system.

Description of Related Art

Ultrasound imaging refers to the use of an ultrasonic probe to emit ultrasonic waves to an object to be scanned. The ultrasonic waves interact with the object to be scanned by reflection, scattering, diffraction, etc. Then, ultrasonic echoes are detected, and the echo data is analyzed and processed to obtain an ultrasound reflection image. Ultrasound imaging technology is widely applied to clinical medical detection such as ophthalmology, obstetrics and gynecology, and gastroenterology. Compared with other imaging modes, clinical ultrasound detection has the advantages of no radiation to the human body, low detection cost, real-time imaging, etc. In the past twenty to thirty years, with the improvement of ultrasonic probe manufacturing and processing technique and the rapid development of computer technology, ultrasonic tomography imaging technology has made considerable progress. Ultrasonic tomography imaging technology uses the ultrasonic probe to emit ultrasonic waves while detecting ultrasonic echoes scattered from an object to be imaged and reconstructing various acoustic parameters, including a reflection map, a sound velocity map, and an attenuation map, according to the echo data.

Ultrasonic tomography imaging belongs to the field of ultrasound imaging, which also needs to use ultrasonic excitation to receive echoes. The differences are that the receiving aperture of ultrasonic tomography imaging is much greater than that of ordinary B-ultrasound, and transmission echoes may be obtained, thereby deriving more imaging modes. However, the amount of data obtained is greater and the computing complexity is higher.

Ultrasonic tomography imaging generally uses the excitation collection mode of emission by a single array element and receiving by all other array elements. Due to the large number of array elements and large receiving aperture, ultrasonic tomography imaging has higher spatial resolution. After completing a single section scan, the motor moves for a distance and then stands still, each array element on the ring array is sequentially excited, all array elements receive at the same time, and the second layer scan is completed. The process is repeated to realize scan imaging of a three-dimensional space. In the field of X-ray tomography imaging scan, such scan is referred to as step scan. Such method requires repeated steps and stops, which easily causes shaking of an ultrasonic transmission medium, resulting in an artifact. Also, since the scan needs to be stopped before moving, the three-dimensional scanning time is very long, which greatly affects the comfort of the patient. On the other hand, tomography imaging of step scan can only reflect the section information of a specific position when the motor stops, and accurate data between sections cannot be obtained, which may cause missed diagnosis and also cause the resolution obtained in the Z-axis direction of an image obtained by such method to be lower. At present, the mainstream tomography imaging scanning method is mainly based on the step manner. A new three-dimensional scan is urgently needed to shorten the scanning time and improve the Z-axis resolution.

SUMMARY

In view of the defects of the current mainstream tomography imaging step scan, the objective of the disclosure is to provide a spiral ultrasonic tomography imaging method and system, which controls the changes in positions of emission array elements during an ultrasonic scanning process, so that the emission array elements are emitted in a spiral trajectory or an approximate spiral trajectory. The new spiral ultrasonic tomography three-dimensional scanning method and the corresponding system obtained may realize rapid continuous uninterrupted data acquisition to ensure that higher spatial resolution is obtained in the Z-axis direction. Multiple layers of redundant data may also be used to improve the signal-to-noise ratio of an image.

In order to realize the above objective, according to an aspect of the disclosure, a spiral ultrasonic tomography imaging method is provided. Under the premise of a uniform displacement of the ultrasonic probe along the Z axis, the method uses the synchronous rotation of the ultrasonic probe or cyclic switching of emission array elements in the ultrasonic probe according to a preset clock direction, so that the change trajectory of the positions of emission array elements over time in a three-dimensional space at each ultrasonic emission time is distributed along a spiral line or along a curve mainly composed of multiple parts of the spiral line. During the process of the uniform displacement of the ultrasonic probe along the Z axis, the ultrasonic probe emits ultrasonic waves and receives and collects echo data. The collected echo data is stored and post-processed to realize ultrasonic tomography imaging of an object to be detected.

The ultrasonic probe includes multiple array elements. Each time an ultrasonic wave is emitted, one of the array elements serves as an emission array element, and the other array elements all serve as receiving array elements. The echo data received by each receiving array element carries tomography imaging information of a local area of the object to be detected near a plane where the ultrasonic probe is located.

The ultrasonic probe specifically:
(i) Performs the uniform displacement along the Z axis along a preset Z-axis direction and at a preset displacement rate while the ultrasonic probe maintains rotation according to a preset rotational angular velocity, and a vector of the rotational angular velocity remains constant; or
(ii) Performs the uniform displacement along the Z axis along a preset Z-axis direction and at a preset displacement rate while the ultrasonic probe maintains rotation according to a preset rotational angular velocity, the magnitude of a vector of the rotational angular velocity remains constant, and the direction of the vector is switched according to a preset switching frequency; or (iii) Performs the uniform displacement along the Z axis along a preset Z-axis direction and at a preset displacement rate while the emission array elements in the ultrasonic probe are maintained to be cyclically switched according to a preset fixed clock direction, and the frequency of switching the emission array elements satisfies a preset requirement; or (iv) Performs the uniform displacement along the Z axis along a preset Z-axis direction and at a preset displacement rate while the emission array elements in the ultrasonic probe are maintained to be cyclically switched according to a preset changing clock direction, the frequency of switching the emission array elements satisfies a preset requirement, and the frequency of changes in the clock direction also satisfies a preset requirement.

The data post-processing specifically includes the following steps. The stored echo data is rearranged and encoded, so that the echo data is arranged according to an order received by the ultrasonic probe. Then, computation and reconstruction are performed to obtain each tomogram. Then, each tomogram is sequentially arranged to perform three-dimensional reconstruction. Finally, logarithmic compression and color or gray-scale mapping are performed to obtain a three-dimensional image. The tomogram is any one of a reflection reconstruction tomogram, a sound velocity reconstruction tomogram, and an attenuation coefficient reconstruction tomogram.

As a further preference of the disclosure, during the process of the uniform displacement of the ultrasonic probe along the Z axis, the ultrasonic probe sequentially excites and emits ultrasonic waves at equal time intervals, or the ultrasonic probe sequentially excites and emits the ultrasonic waves according to preselected partial array elements.

As a further preference of the disclosure, the ultrasonic probe is an annular ultrasonic probe or a concave-array ultrasonic probe with multiple uniformly distributed array elements.

As a further preference of the disclosure, for the cyclic switching of the emission array elements in the ultrasonic probe according to a preset clock direction, the switching involves switching several adjacent array elements in the annular ultrasonic probe or involves switching several array elements at fixed intervals in the annular ultrasonic probe.

As a further preference of the disclosure, for the cyclic switching of the emission array elements in the ultrasonic probe according to the preset clock direction, the switching involves switching all array elements in the annular ultrasonic probe.

According to another aspect of the disclosure, the disclosure provides a spiral ultrasonic tomography imaging device, which includes an ultrasonic probe, a Z-axis movement subsystem, a memory, and a data post-processing module.

The Z-axis movement subsystem is used to drive a uniform displacement of the ultrasonic probe along the Z axis and to enable the ultrasonic probe to synchronously rotate, so that the change trajectory of the positions of emission array elements over time in a three-dimensional space at each ultrasonic emission time is distributed along a spiral line or along a curve mainly composed of multiple parts of the spiral line.

The ultrasonic probe is used to emit ultrasonic waves and receive and collect echo data during the process of the uniform displacement of the ultrasonic probe along the Z axis. The ultrasonic probe includes multiple array elements. Each time an ultrasonic wave is emitted, one of the array elements serves as an emission array element, and the other array elements all serve as receiving array elements. The echo data received by each receiving array element carries tomography imaging information of a local area of the object to be detected near a plane where the ultrasonic probe is located.

The ultrasonic probe performs the uniform displacement along the Z axis driven by the Z-axis movement subsystem along a preset Z-axis direction and at a preset displacement rate while the ultrasonic probe maintains rotation according to a preset rotational angular velocity, and a vector of the rotational angular velocity remains constant. Alternatively, the ultrasonic probe performs the uniform displacement along the Z axis along a preset Z-axis direction driven by the Z-axis movement subsystem, and at a preset displacement rate while the ultrasonic probe maintains rotation according to a preset rotational angular velocity, the magnitude of a vector of the rotational angular velocity remains constant, and the direction of the vector is switched according to a preset switching frequency.

The memory is used to store echo data collected by the ultrasonic probe.

The data post-processing module is used to rearrange and encode the stored echo data, so that the echo data is arranged according to the order received by the ultrasonic probe. Then, computation and reconstruction are performed to obtain each tomogram. Then, each tomogram is sequentially arranged to perform three-dimensional reconstruction. Finally, logarithmic compression and color or gray-scale mapping are performed to obtain a three-dimensional image. The tomogram is any one of a reflection reconstruction tomogram, a sound velocity reconstruction tomogram, and an attenuation coefficient reconstruction tomogram.

According to another aspect of the disclosure, the disclosure provides a spiral ultrasonic tomography imaging device, which includes an ultrasonic probe, a Z-axis movement subsystem, a memory, and a data post-processing module.

The Z-axis movement subsystem is used to drive a uniform displacement of the ultrasonic probe along the Z axis.

Emission array elements in the ultrasonic probe can be cyclically switched according to a preset clock direction, so that the change trajectory of the positions of the emission array elements over time in a three-dimensional space at each ultrasonic emission time is distributed along a spiral line or along a curve mainly composed of multiple parts of the spiral line. The ultrasonic probe is used to emit ultrasonic waves and receive and collect echo data during the process of the uniform displacement of the ultrasonic probe along the Z axis. The ultrasonic probe includes multiple array elements. Each time an ultrasonic wave is emitted, one of the array elements serves as an emission array element, and the other array elements all serve as receiving array elements. The echo data received by each receiving array element carries tomography imaging information of a local area of an object to be detected near a plane where the ultrasonic probe is located.

The ultrasonic probe performs the uniform displacement along the Z axis along a preset Z-axis direction can be driven by the Z-axis movement subsystem and at a preset displacement rate while the emission array elements in the ultrasonic probe are maintained to be cyclically switched according to a preset fixed clock direction, and the frequency of switching the emission array elements satisfies a preset requirement.

Alternatively, the ultrasonic probe performs the uniform displacement along the Z axis along a preset Z-axis direction driven by the Z-axis movement subsystem and at a preset displacement rate while the emission array elements in the ultrasonic probe are maintained to be cyclically switched according to a preset changing clock direction, the frequency of switching the emission array elements satisfies a preset requirement, and the frequency of changes in the clock direction also satisfies a preset requirement.

The memory is used to store echo data collected by the ultrasonic probe.

The data post-processing module is used to rearrange and encode the stored echo data, so that the echo data is arranged according to the order received by the ultrasonic probe. Then, computation and reconstruction are performed to obtain each tomogram. Then, each tomogram is sequentially arranged to perform three-dimensional reconstruction. Finally, logarithmic compression and color or gray-scale mapping are performed to obtain a three-dimensional image. The tomogram is any one of a reflection reconstruction tomogram, a sound velocity reconstruction tomogram, and an attenuation coefficient reconstruction tomogram.

As a further preference of the disclosure, the spiral ultrasonic tomography imaging device further includes a bed. The bed is used to carry the object to be detected, and can preferably provide water as an ultrasonic coupling agent between the ultrasonic probe and the object to be detected.

As a further preference of the disclosure, the spiral ultrasonic tomography imaging device further includes a water treatment subsystem for filtering impurities in the water as the ultrasonic coupling agent, removing bubbles in the water, and controlling water circulation.

Through the above technical solutions conceived in the disclosure, compared with the prior art, the array elements of the spiral tomography imaging method and system provided by the disclosure are sequentially emitted in a spiral trajectory or an approximate spiral trajectory (the spiral trajectory may be, for example, a spiral line with fixed pitch; and the approximate trajectory may be, for example, a curve composed of multiple parts of the spiral line), and the echo data is received. The scanning process is continuous, and the acquired echo data covers the entire three-dimensional space, thereby greatly improving the resolution and contrast in the Z-axis direction, improving the quality of ultrasonic tomography imaging while shortening the scanning time, reducing artifacts, and improving the comfort of the patient, which is conducive to the promotion and application of the equipment.

In the disclosure, the ultrasonic probe is used to generate ultrasonic waves. After the ultrasonic waves interact with the object to be imaged by reflection, transmission, etc., the ultrasonic probe may also be used to receive the echo after the action. Similar to conventional ultrasound detection, after each excitation and emission of an ultrasonic wave, after a short delay, the collection system starts to receive the echoes and records sufficient signal length while transmitting the echo data to a computing server after encoding. The server decodes multiple layers of echo data and rearranges according to the actual emission sequence of the physical array elements. The disclosure may further calculate to obtain the position of an array element in a space at each emission time according to the movement speed of the probe and the emission time interval of the array elements, so as to complete the precise modeling of the coordinate system, and realize the spiral trajectory ultrasonic tomography reconstruction process by referring to the reconstruction method of a two-dimensional ultrasound image. In addition, the subsequent data post-processing may be performed asynchronously, thereby reducing the time for applying the ultrasound detection process to the object to be detected. After the scan is completed and the echo data is stored, the stored echo data may be separately post-processed.

DETAILED DESCRIPTION OF DISCLOSED EMBODIMENTS

For the objective, technical solutions, and advantages of the disclosure to be clearer, the disclosure is further described in detail below with reference to the accompanying drawings and the embodiments. It should be understood that the specific embodiments described here are only used to explain the disclosure, but not to limit the disclosure. In addition, the technical features involved in the various embodiments of the disclosure described below may be combined with each other as long as there is no conflict therebetween.

An ultrasonic tomography imaging method based on spiral trajectory scan in the disclosure may be performed according to the following steps during specific operation:

S1: Acquire external input information and set scanning parameters, including pitch, emission mode, encoding method, number of scanning layers, etc.

Taking the probe as an annular probe as an example, any of the following 3 methods may be adopted to obtain a spiral trajectory line of emission array elements.

i. The emission array elements remain unchanged. The whole probe moves along the Z axis while rotating around the Z axis according to a preset fixed clock direction. For example, when the fixed clock direction is preset to a counterclockwise direction, the whole probe moves along the Z axis while rotating around the Z axis in the counterclockwise direction. A clockwise direction may be deduced by analogy.

ii. The emission array elements remain unchanged. The whole probe moves along the Z axis while rotating around the Z axis according to, for example, clock periodic changes of counterclockwise-clockwise-counterclockwise. Each time when a pitch is reached, the clock direction of rotation is changed once. For example, the whole probe moves along the Z axis while rotating around the Z axis according to the changing clock direction of first the counterclockwise direction, then the clockwise direction, and then the counterclockwise direction to change the clock direction of rotation.

iii. The probe only moves along the Z axis. Emission array elements are cyclically switched according to a preset fixed clock direction (for example, the counterclockwise direction) (note that the direction of the ultrasonic probe moving along the Z axis is the positive direction of the Z axis, the switching of the counterclockwise direction satisfies the right-hand rule, and the switching of the clockwise direction satisfies the left-hand rule).

iv. The probe only moves along the Z axis. Emission array elements are cyclically switched according to a preset changing clock direction (for example, counterclockwise-clockwise-counterclockwise changing periodically). The frequency of switching the array elements may be preset, and the frequency of changes in the clock direction may also be preset. The frequency of switching the array elements may be an integer multiple of the frequency of changes in the clock direction.

When adopting method i., the pitch is related to the translation speed and the rotational angular velocity, and is also affected by the translation speed and the rotational angular velocity. Moreover, a rotation angle α of each layer can only be equal to 360 degrees, and the correspondingly obtained trajectory line of the emission array elements are distributed along a complete spiral line.

When adopting method ii., the pitch is related to the translation speed and the rotational angular velocity, and is also affected by the translation speed and the rotational angular velocity. The rotation angle α of each layer may be equal to 360 degrees or less than 360 degrees, and the correspondingly obtained trajectory line of the emission array elements are composed of multiple parts of a spiral line.

When adopting methods iii. and iv., the pitch is related to the translation speed and the frequency of switching the array elements, and is also affected by the translation speed and the frequency of switching the array elements. At this time, the rotation angle α of each layer may be equal to 360 degrees or less than 360 degrees, and the correspondingly obtained trajectory line of the emission array elements are distributed along a complete spiral line or along parts of the spiral line.

In addition, for the ultrasonic probe, ultrasonic waves may be sequentially excited and emitted at equal time intervals, or partial array elements in the probe may be preselected to sequentially excite and emit the ultrasonic waves, that is, the ultrasonic waves may be sequentially excited and emitted according to the preselected partial array elements.

S2: An industrial control computer sends an excitation collection command. An excitation collection system starts to emit ultrasonic waves and receive echo data.

S3: A storage and computing server receives and saves original data transmitted by the collection system for subsequent processing.

S4: The server rearranges and decodes the received original data, so that the echo data is arranged according to the order received by the physical probe. A reconstruction algorithm is used to reconstruct a tomogram, including a reflection map, a sound velocity map, and an attenuation map.

S5: Post-process the tomogram, such as enhancing the contrast. Then, the tomogram is mapped and visualized according to a pre-saved color table, and finally three-dimensionally reconstructed and displayed.

Correspondingly, an ultrasonic tomography imaging system based on spiral trajectory scan of the disclosure may include an ultrasonic probe, a motion control subsystem, an excitation collection subsystem, and a computing server.

The ultrasonic probe is used to generate ultrasonic waves. After the ultrasonic waves interact with an object to be imaged by reflection, transmission, etc., the ultrasonic probe may also be used to receive the echo after the action.

The motion control subsystem is used to control the probe to move along the Z axis at a constant speed, thereby continuously acquire three-dimensional ultrasonic echo information of the object to be imaged.

The excitation collection subsystem is used to generate high-voltage excitation signals to drive the probe to generate the ultrasonic waves. The collection subsystem is used to collect echo signals to be digitized and transmitted to the server.

The computing server may be used to receive echo data packets sent by the collection system, decode and rearrange data formats. Then, the algorithm is used to reconstruct an ultrasonic tomography image. Finally, multiple layers of tomograms are used to reconstruct a three-dimensional image.

The ultrasonic probe may sequentially excite and emit the ultrasonic waves at equal time intervals, and coordinated with the motion control subsystem, the ultrasonic probe is driven to move along the Z axis, etc., so that the movement trajectory of the emission array elements is spiral or approximately spiral. After each excitation, after a short delay, the collection system starts to receive the echoes and records sufficient signal length while transmitting the echo data to the computing server after encoding. The server decodes multiple layers of echo data and rearranges according to the actual emission sequence of the physical array elements. According to the movement speed of the probe and the emission time interval of the array elements, the position of an array element in a space at each emission time is calculated and obtained, so as to complete the precise modeling of the coordinate system, and realize the spiral trajectory ultrasonic tomography reconstruction process by referring to the reconstruction method of a two-dimensional ultrasound image.

In addition to the above components, the ultrasonic tomography imaging system based on spiral trajectory scan may also be disposed with other supporting components, such as a bed, a water treatment subsystem, and an industrial control computer.

The bed is used to carry various components of the system, and is also used to carry an object to be scanned. Since there is a distance between the probe and the object to be scanned, it is necessary to use a water medium as an ultrasonic coupling agent. The water treatment system is used to filter impurities in the water of the coupling agent, remove bubbles in the water, and control water circulation. The industrial control computer may be used as the control center of the entire system, and may also be used as a human-machine interaction interface, undertaking the tasks of controlling and coordinating the components.

Embodiment 1

Figure 1A:
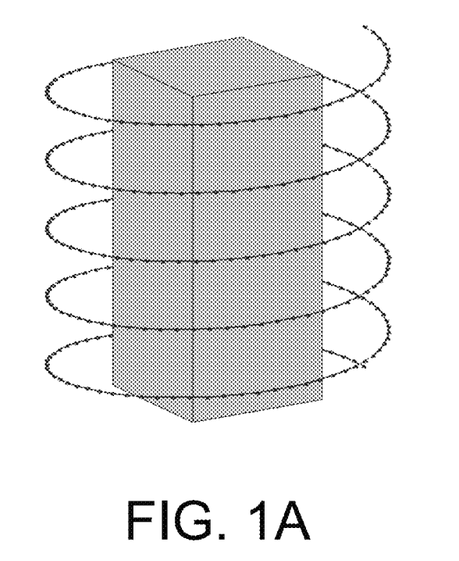
FIG. 1A is a schematic view of a movement trajectory of an emission array element in Embodiment 1 of the disclosure.
Figure 1B:
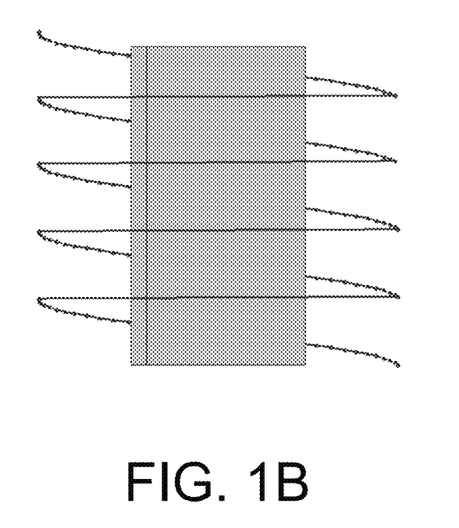
FIG. 1B is a schematic view of a movement trajectory of another emission array element in Embodiment 1 of the disclosure.

This embodiment provides a spiral trajectory ultrasonic tomography imaging method, which is used to perform ultrasonic three-dimensional imaging of mammary gland. As shown in FIG. 1A, the spiral trajectory scan adopted by the disclosure may be used to mechanically move emission array elements to form a spiral trajectory, or move an annular probe toward the Z-axis direction, and then sequentially excite array elements on the ring, so that the movement trajectory of the emission array elements spirally cover an entire three-dimensional imaging area. In addition, in the spiral trajectory scan adopted by the disclosure, the next layer may be directly scanned without completing 360-degree rotation by the movement trajectory of the emission array elements. As shown in FIG. 1B, the trajectory of the emission array elements moves by 50 degrees for each movement of a pitch.

Figure 2:
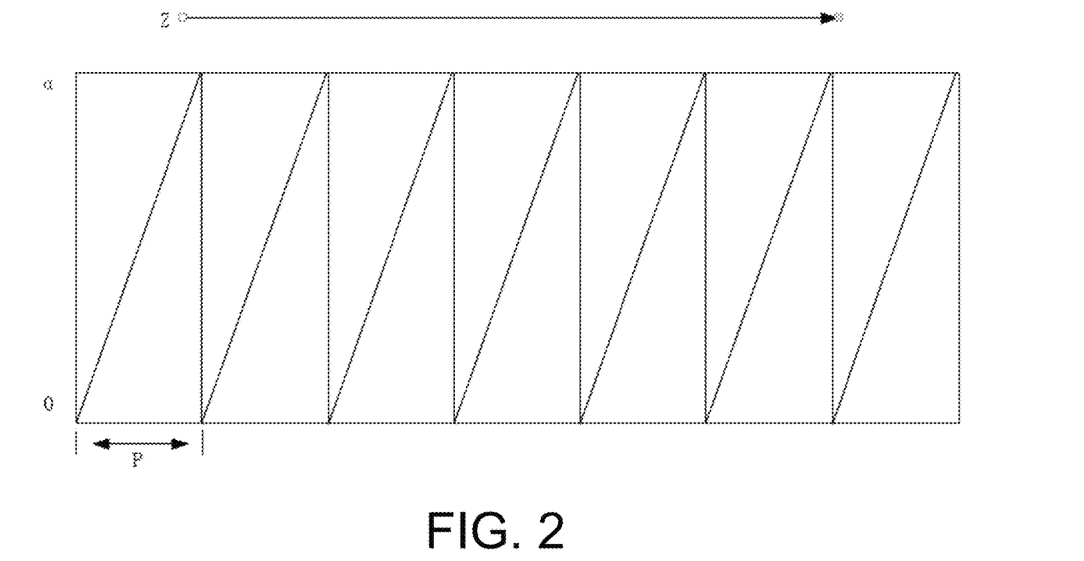
FIG. 2 is a plan view of a spiral trajectory of Embodiment 1 of the disclosure.

For a deeper understanding of an approximate spiral trajectory, it may be assumed that the number of scanning layers is 7, the pitch is P, and the rotation angle of each layer of excitation array elements is $\alpha$ ($\alpha$ may be set as 50 degrees, and may, of course, also be other values less than or equal to 360 degrees according to requirements), as shown in FIG. 2.

Figure 3:
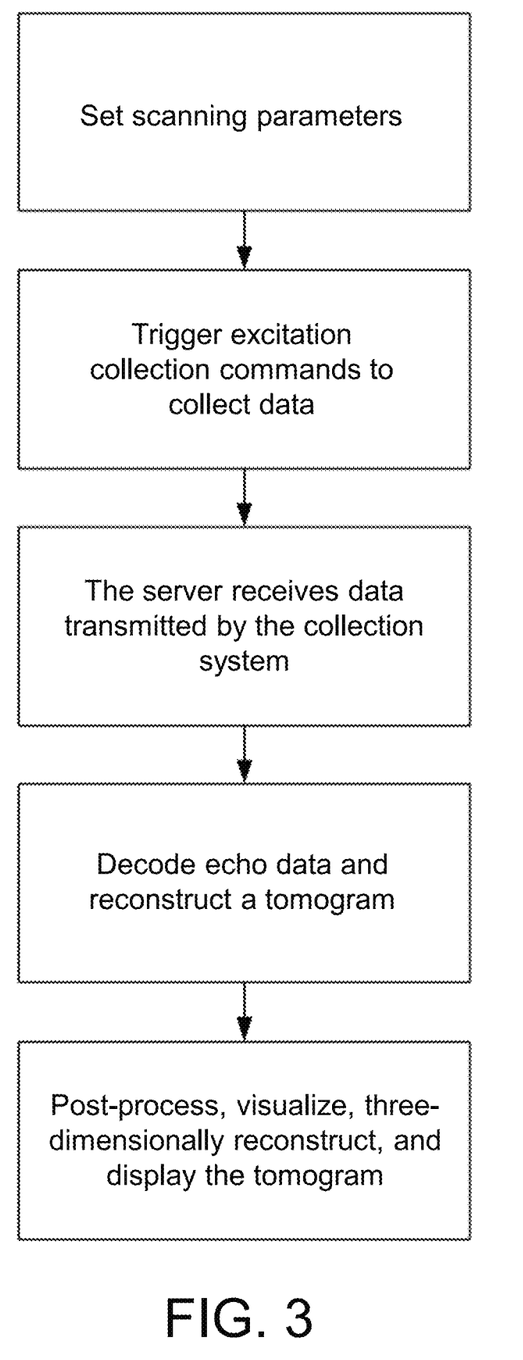
FIG. 3 is a flowchart of a spiral trajectory ultrasonic tomography imaging method in Embodiment 1 of the disclosure.

The method provided by the disclosure may be executed by an ultrasonic imaging device, referring to FIG. 3, the method includes:

S1: Set scanning parameters.

Specifically, after an object to be scanned is placed in an imaging range, the user may input various scanning parameters, including pitch, emission mode, encoding method, number of scanning layers, etc., into an industrial control screen. An industrial control computer transmits the parameters to a motor, an excitation collection system, a server, and other components to complete the preparatory work before scan.

S2: Trigger excitation collection commands to collect data.

Specifically, the industrial control computer sends a command to a motor driver. The motor starts to move at a preset constant speed c. At the same time, the industrial control computer sends a command to the excitation collection system. The excitation collection system starts to emit ultrasonic waves and receive echo data. After the number of scanning layers specified by the user is completed, data collection is stopped, the movement of the motor is stopped, and the motor restores to an initial position.

S3: The server receives data transmitted by the collection system.

Specifically, the server activates a daemon process in advance before starting the scan to monitor whether there are data packets on the line. Original data is collected and then saved in a local hard disk for subsequent processing. The server may be a single node, may be composed of distributed multi-node servers, or may be a general-purpose computer with computing capabilities, and the specific form thereof is not limited in the disclosure.

S4: Decode data and reconstruct a tomogram.

Specifically, the server rearranges and decodes the received original data, so that the echo data is arranged into the actual physical sequence. An ultrasonic reconstruction algorithm, such as delay superposition, back projection, and waveform inversion, is used to reconstruct the tomogram, including a reflection map, a sound velocity map, and an attenuation map.

S5: The tomogram is post-processed, visualized, three-dimensionally reconstructed, and displayed.

Specifically, the tomogram is post-processed, such as enhancing the contrast. Then, the tomogram is mapped and visualized according to a pre-saved color table, and finally three-dimensionally reconstructed and displayed.

Embodiment 2

Figure 4:
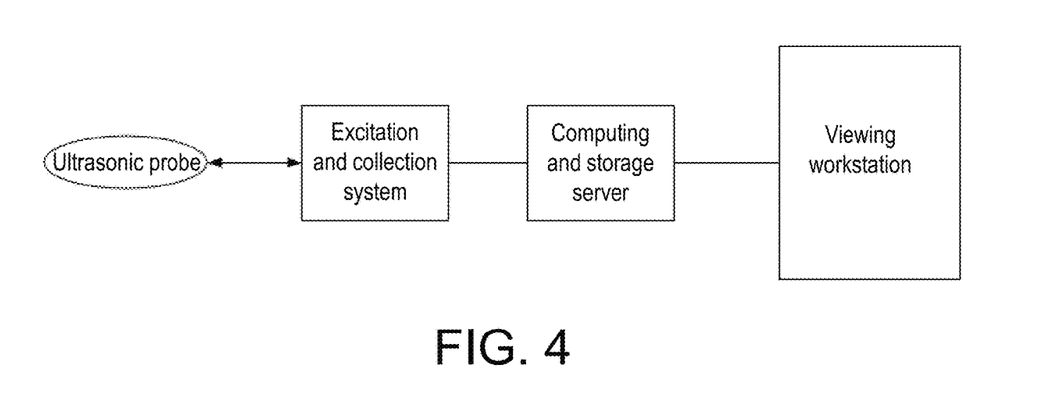
FIG. 4 is a schematic view of a system composition of a spiral trajectory imaging system of Embodiment 2 of the disclosure.

This embodiment provides a spiral trajectory ultrasonic tomography imaging system. Referring to FIG. 4, the system includes an ultrasonic probe, an excitation and collection subsystem, a computing and storage server, and a viewing workstation. The ultrasonic probe is an ultrasonic generator and an ultrasonic sensor, and is used to generate ultrasonic waves. After the ultrasonic waves interact with an object to be imaged by reflection, transmission, etc., the ultrasonic probe may also be used to receive echoes after the action. The excitation and collection system is used to generate high-voltage excitation signals to drive the probe to generate the ultrasonic waves. The collection system is used to collect echo signals to be digitized and transmitted to the server. The computing and storage server is used to receive echo data packets sent by the collection system, decode and rearrange data formats. Then, an algorithm is used to reconstruct an ultrasonic tomography image. Finally, multiple layers of tomograms are used to reconstruct a three-dimensional image. The viewing workstation receives a reconstructed slice image transmitted from the computing and storage server and is used to display an image. The user of the equipment views image data from the viewing workstation to understand internal information of a scanned object.

Figure 5:
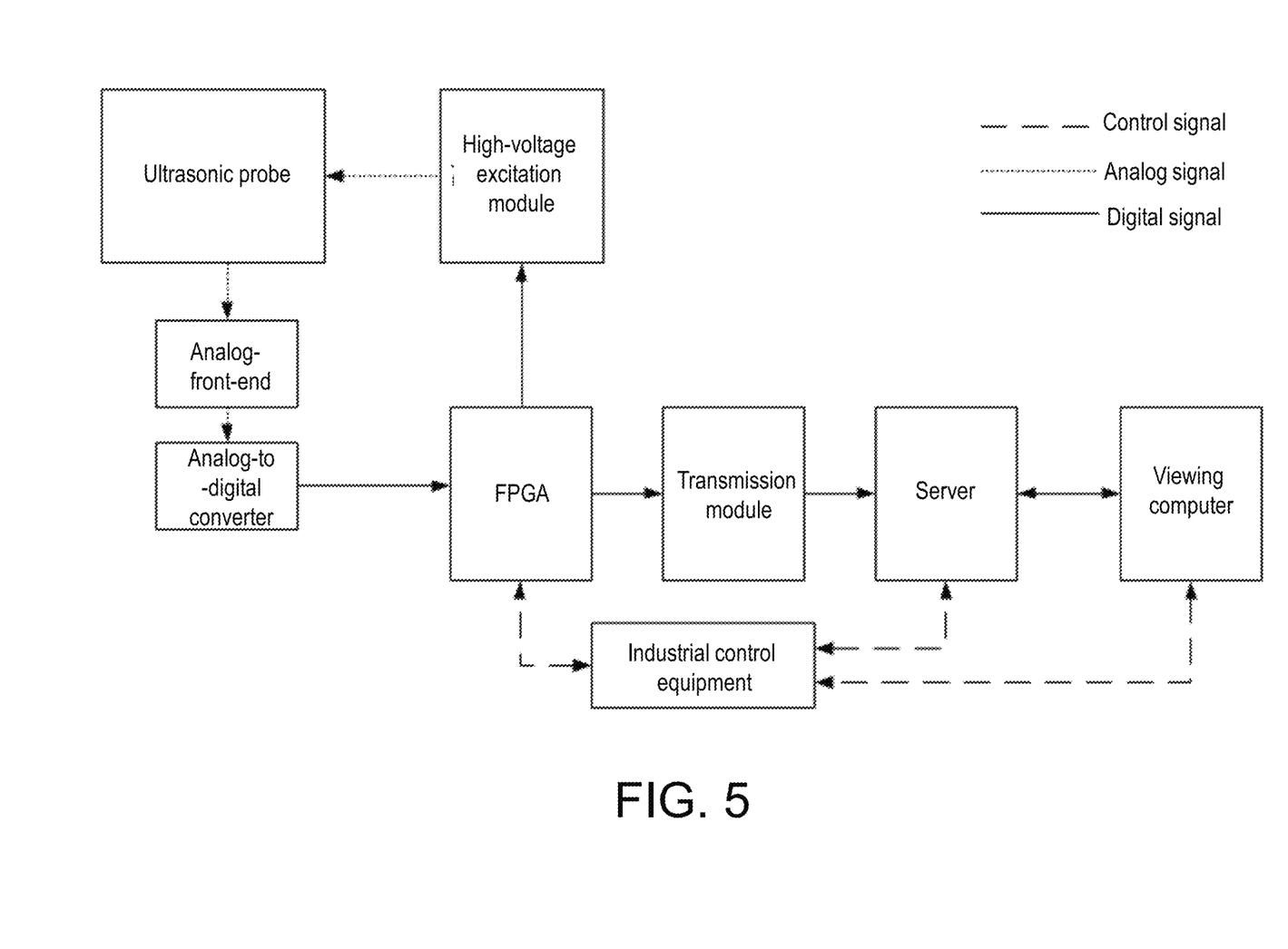
FIG. 5 is a schematic view of signal and data flow of a system of Embodiment 2 of the disclosure.

FIG. 5 shows signal and data flow of the spiral trajectory ultrasonic tomography imaging system provided by the disclosure. The excitation and collection subsystem undertakes most of the signal and data processing process. The core components of the subsystem include an FPGA, an analog-to-digital converter, an analog front-end circuit, a high-voltage excitation module, a transmission module, etc. The FPGA is responsible for configuring parameters of other submodules in the subsystem, coordinating cooperative work of various submodules, and completing work such as analog-to-digital conversion, data repackaging, data shunting, and data transmission. User-related equipment mainly include input and output industrial control equipment and viewing computer. The industrial control computer needs to communicate with the FPGA, a computing server, and a viewing server.

Figure 6A:
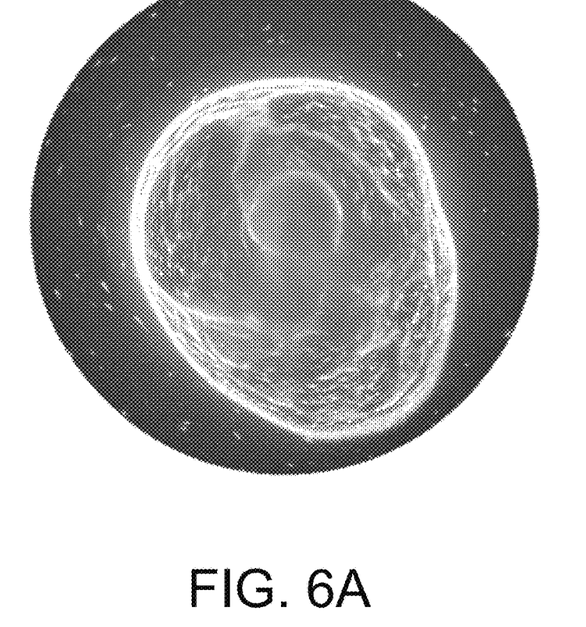
FIG. 6A is a diagram of a reconstructed thigh slice in Embodiment 2 of the disclosure.
Figure 6B:
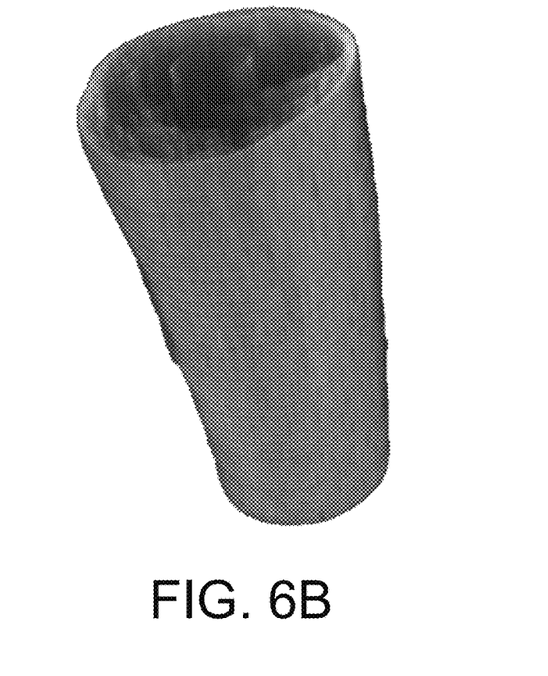
FIG. 6B is a three-dimensional view of a reconstructed thigh in Embodiment 2 of the disclosure.

Taking the scan of a human thigh as an example, the process of using this system to scan and generate an image is as follows:

The probe is immersed in the liquid coupling agent. The thigh to be scanned is passed through the annular probe and statically placed in the middle position. The daemon process of the storage and computing server is turned on. The human-machine interaction interface on the industrial control computer is used to set parameters, such as the thickness of a scanning layer, the number of layers, and the emission mode. After confirming that there is no mistake, the scan starts. When prompted that the scan is completed, a reconstructed slice image and a three-dimensional image may be viewed on the viewing server, as shown in FIG. 6A and FIG. 6B.

In the ultrasonic tomography imaging method and device based on spiral trajectory scan of the disclosure, the detailed technologies involved, such as the movement control method, the excitation method of the ultrasonic probe, the echo collection method, the data recombination method, and the tomographic reconstruction method, may all be set by referring to the relevant existing technologies unless otherwise specified. For example, in terms of movement control, an ordinary stepping or servo motor may be used to drive the ultrasonic probe to move toward the Z-axis direction at a certain constant speed before ultrasonic emission starts, and to stop the movement after ultrasonic echo collection is completed.

Persons skilled in the art may easily understand that the above are only the preferred embodiments of the disclosure and are not intended to limit the disclosure. Any modification, equivalent replacement, improvement, etc. made within the spirit and principle of the disclosure should be included in the protection scope of the disclosure.

What is claimed is:

1. A spiral ultrasonic tomography imaging method with an ultrasonic probe, the ultrasonic probe comprises a plurality of array elements, the spiral ultrasonic tomography imaging method, comprising:

under a premise of a uniform displacement of the ultrasonic probe along a Z axis, using synchronous rotation of the array elements or performing cyclic switching of a change trajectory linked by positions of an emission array element selected from one of the array elements in the ultrasonic probe according to a preset fixed spiral direction or a preset changing spiral direction each time, so that the change trajectory of positions of the emission array element over time in a three-dimensional space at each ultrasonic emission time is distributed along a spiral line or along a curve composed of a plurality of parts of the spiral line; and during a process of the uniform displacement of the ultrasonic probe along the Z axis, emitting, by the ultrasonic probe, an ultrasonic wave and receiving and collecting, by the ultrasonic probe, echo data, and the echo data been collected is stored and post-processed to realize ultrasonic tomography imaging of an object to be detected, wherein the array elements of the ultrasonic probe are located outside the object to be detected, each time the ultrasonic wave is emitted, one of the array elements serves as the emission array element, and the other array elements all serve as receiving array elements, each array element of the ultrasonic probe has functions of the emission array element and a receiving array element among the receiving array elements, and the echo data received by each of the receiving array elements carries tomography imaging information of a local area of the object to be detected near a plane where the ultrasonic probe is located;

wherein the ultrasonic probe is a concave-array ultrasonic probe with the plurality of array elements, the ultrasonic probe performs at least one of steps (a) and (b) or a combination thereof:

(a) performing, by the ultrasonic probe, the uniform displacement along the Z axis along a preset Z-axis direction and at a preset displacement rate while the emission array element in the ultrasonic probe is maintained to be cyclically switched according to the preset fixed spiral direction, and a frequency of switching the emission array element among the array elements satisfies a preset requirement;

(b) performing, by the ultrasonic probe, the uniform displacement along the Z axis along the preset Z-axis direction and at the preset displacement rate while the emission array element in the ultrasonic probe is maintained to be cyclically switched according to the preset changing spiral direction, the frequency of switching the emission array element among the array elements satisfies the preset requirement, and a frequency of changes in the preset fixed spiral direction or in the preset changing spiral direction also satisfies the preset requirement, and wherein performing data post-processing by:

rearranging and encoding the echo data been stored, so that the echo data is arranged according to an order received by the ultrasonic probe;

computing and reconstructing to obtain each tomogram;

sequentially arranging each tomogram to perform three-dimensional reconstruction, and;

performing logarithmic compression and color or gray-scale mapping to obtain a three-dimensional image, wherein the tomogram is one of a reflection reconstruction tomogram, a sound velocity reconstruction tomogram, and an attenuation coefficient reconstruction tomogram, or a combination thereof.

2. The spiral ultrasonic tomography imaging method according to claim 1, wherein during the process of the uniform displacement of the ultrasonic probe along the Z axis, the ultrasonic probe sequentially excites and emits the ultrasonic wave at equal time intervals, or the ultrasonic probe sequentially excites and emits the ultrasonic wave according to preselected partial array elements.

3. A spiral ultrasonic tomography imaging device, comprising an ultrasonic probe, a Z-axis movement motor, a memory, and a processor, wherein the Z-axis movement motor is configured to drive a uniform displacement of the ultrasonic probe along a Z axis and to enable the ultrasonic probe to synchronously rotate, so that a change trajectory of positions of an emission array element over time in a three-dimensional space at each ultrasonic emission time is distributed along a spiral line or along a curve composed of a plurality of parts of the spiral line;

the ultrasonic probe is configured to emit an ultrasonic wave and receive and collect echo data during a process of the uniform displacement of the ultrasonic probe along the Z axis;

the ultrasonic probe comprises a plurality of array elements, each time the ultrasonic wave is emitted, one of the array elements serves as the emission array element, and the other array elements all serve as receiving array elements, the echo data receivedby each of the receiving array elements carries tomography imaging information of a local area of an object to be detected near a plane where the ultrasonic probe is located;

wherein the ultrasonic probe is a concave-array ultrasonic probe with the plurality of array elements, the array elements of the ultrasonic probe are located outside the object to be detected each array element of the ultrasonic probe has functions of the emission array element and a receiving array element among the receiving array elements, and the echo data received by each of the receiving array elements carries tomography imaging information of a local area of the object to be detected near a plane where the ultrasonic probe is located, the ultrasonic probe performs the uniform displacement along the Z axis along a preset Z-axis direction driven by the Z-axis movement motor and at a preset displacement rate while the emission array element in the ultrasonic probe is maintained to be cyclically switched according to a preset fixed spiral direction, and a frequency of switching the emission array element among the array elements satisfies a preset requirement; or the ultrasonic probe performs the uniform displacement along the Z axis along the preset Z-axis direction driven by the Z-axis movement motor and at the preset displacement rate while the emission array element in the ultrasonic probe is maintained to be cyclically switched according to a preset changing spiral direction, the frequency of switching the emission array element among the array elements satisfies the preset requirement, and a frequency of changes in the preset fixed spiral direction or in the preset changing spiral direction also satisfies the preset requirement;

the memory is configured to store the echo data collected by the ultrasonic probe; and the processor is configured to rearrange and encode the echo data been stored, so that the echo data is arranged according to an order received by the ultrasonic probe, the processor is further configured to compute and reconstruct to obtain each tomogram, sequentially arrange each tomogram to perform three-dimensional reconstruction, and perform logarithmic compression and color or gray-scale mapping to obtain a three-dimensional image; wherein the tomogram is one of a reflection reconstruction tomogram, a sound velocity reconstruction tomogram, and an attenuation coefficient reconstruction tomogram, or a combination thereof.

4. A spiral ultrasonic tomography imaging device, comprising an ultrasonic probe, a Z-axis movement motor, a memory, and a processor, wherein the Z-axis movement motor is configured to drive a uniform displacement of the ultrasonic probe along a Z axis;

the ultrasonic probe comprises a plurality of array elements, each array element of the ultrasonic probe has functions of an emission array element and a receiving array element among receiving array elements, the array elements of the ultrasonic probe are located outside an object to be detected, the emission array element selected from one of the array elements in the ultrasonic probe can be cyclically switched according to a preset fixed spiral direction or a preset changing spiral direction, so that a change trajectory of positions of the emission array element over time in a three-dimensional space at each ultrasonic emission time is distributed along a spiral line or along a curve composed of a plurality of parts of the spiral line;

each time an ultrasonic wave is emitted, one of the array elements serves as the emission array element, and the other array elements all serve as the receiving array elements, and echo data received by each of the receiving array elements carries tomography imaging information of a local area of the object to be detected near a plane where the ultrasonic probe is located, the ultrasonic probe is configured to emit the ultrasonic wave and receive and collect the echo data during a process of the uniform displacement of the ultrasonic probe along the Z axis;

wherein the ultrasonic probe is a concave-array ultrasonic probe with the plurality of array elements, the ultrasonic probe performs the uniform displacement along the Z axis along a preset Z-axis direction driven by the Z-axis movement motor and at a preset displacement rate while the emission array element in the ultrasonic probe is maintained to be cyclically switched according to the preset fixed spiral direction, and a frequency of switching the emission array element among the array elements satisfies a preset requirement; or the ultrasonic probe performs the uniform displacement along the Z axis along the preset Z-axis direction driven by the Z-axis movement motor and at the preset displacement rate while the emission array element in the ultrasonic probe is maintained to be cyclically switched according to the preset changing spiral direction, the frequency of switching the emission array element among the array elements satisfies the preset requirement, and a frequency of changes in the preset fixed spiral direction or in the preset changing spiral direction also satisfies the preset requirement;

the memory is configured to store the echo data collected by the ultrasonic probe; and the processor is configured to rearrange and encode the echo data been stored, so that the echo data is arranged according to an order received by the ultrasonic probe, the processor is further configured to compute and reconstruct to obtain each tomogram, sequentially arrange each tomogram to perform three-dimensional reconstruction, and perform logarithmic compression and color or gray-scale mapping to obtain a three-dimensional image; wherein the tomogram is one of a reflection reconstruction tomogram, a sound velocity reconstruction tomogram, and an attenuation coefficient reconstruction tomogram, or a combination thereof.

5. The spiral ultrasonic tomography imaging device according to claim 3, wherein the spiral ultrasonic tomography imaging device further comprises a bed for carrying the object to be detected and preferably providing water as an ultrasonic coupling agent between the ultrasonic probe and the object to be detected.

6. The spiral ultrasonic tomography imaging device according to claim 5, wherein the spiral ultrasonic tomography imaging device further comprises a water treatment subsystem for filtering impurities in the water as the ultrasonic coupling agent, removing bubbles in the water, and controlling water circulation.

7. The spiral ultrasonic tomography imaging device according to claim 4, wherein the spiral ultrasonic tomography imaging device further comprises a bed for carrying the object to be detected and preferably providing water as an ultrasonic coupling agent between the ultrasonic probe and the object to be detected.

8. The spiral ultrasonic tomography imaging device according to claim 7, wherein the spiral ultrasonic tomography imaging device further comprises a water treatment subsystem for filtering impurities in the water as the ultrasonic coupling agent, removing bubbles in the water, and controlling water circulation.

* * * * *